(12) United States Patent
Heuser et al.

(10) Patent No.: US 7,985,337 B2
(45) Date of Patent: Jul. 26, 2011

(54) DEVICE FOR REMOVING LEUKOCYTES FROM BLOOD

(75) Inventors: Frank Heuser, Wuppertal (DE); Martin König, Düsseldorf (DE); Horst-Dieter Lemke, Obernburg (DE); Bodo Von Harten, Wuppertal (DE)

(73) Assignee: Membrana GmbH, Wuppertal (DE)

( * ) Notice: Subject to any disclaimer, the term of this patent is extended or adjusted under 35 U.S.C. 154(b) by 247 days.

(21) Appl. No.: 12/522,297

(22) PCT Filed: Jan. 10, 2008

(86) PCT No.: PCT/EP2008/000128
§ 371 (c)(1),
(2), (4) Date: Jul. 7, 2009

(87) PCT Pub. No.: WO2008/083965
PCT Pub. Date: Jul. 17, 2008

(65) Prior Publication Data
US 2010/0084331 A1 Apr. 8, 2010

(30) Foreign Application Priority Data
Jan. 13, 2007 (DE) .......................... 10 2007 002 059

(51) Int. Cl.
B01D 63/02 (2006.01)
B01D 61/00 (2006.01)

(52) U.S. Cl. ......... 210/321.88; 210/321.89; 210/500.23; 210/500.21; 210/321.62

(58) Field of Classification Search .......................... None
See application file for complete search history.

(56) References Cited

U.S. PATENT DOCUMENTS

| | | | | |
|---|---|---|---|---|
| 4,882,106 A | * | 11/1989 | Johnson et al. | 264/41 |
| 4,992,332 A | | 2/1991 | Kamei et al. | |
| 5,026,365 A | | 6/1991 | Rossini et al. | |
| 5,143,312 A | * | 9/1992 | Baurmeister | 242/444 |
| 6,498,007 B1 | | 12/2002 | Adachi et al. | |
| 2008/0203024 A1 | * | 8/2008 | Lemke et al. | 210/651 |
| 2009/0060890 A1 | * | 3/2009 | Humes et al. | 424/93.71 |

FOREIGN PATENT DOCUMENTS

| | | |
|---|---|---|
| EP | 0285812 A1 | 10/1988 |
| EP | 0732141 A1 | 9/1996 |
| WO | WO 95/18665 A1 | 7/1995 |
| WO | WO 2007/057065 A1 | 5/2007 |

* cited by examiner

*Primary Examiner* — Krishnan S Menon
(74) *Attorney, Agent, or Firm* — Hammer & Associates, P.C.

(57) ABSTRACT

A device for reducing the number of leucocytes in blood comprising a plurality of hollow fibers based on organic polymers, whereby the hollow fibers have a lumen and a wall surrounding the lumen, said wall having an internal surface facing the lumen and an external surface, whereby the hollow fibers are arranged in a cylindrical housing with an inlet arrangement and an outlet arrangement and whereby an outer space is formed between the hollow fibers and the housing, which space is accessible for a fluid via the inlet arrangement and the outlet arrangement, characterized in that only the external surfaces of the hollow fibers are accessible for a fluid, that the lumina of the hollow fibers are not accessible for a fluid, that the arrangement of the hollow fibers shows a high degree of order and that the hollow fibers based on organic polymers cause a generation of the complement activation product C5a in a concentration of at least 10 μg per m² of fiber surface.

13 Claims, 2 Drawing Sheets

DEVICE FOR REMOVING LEUKOCYTES FROM BLOOD

The invention relates to a device for the removal of leukocytes from blood.

Blood essentially consists of plasma and cellular elements. These include erythrocytes (red blood cells), thrombocytes (platelets), and leukocytes (white blood cells). White blood cells include lymphocytes, monocytes, and neutrophil granulocytes (neutrophils, PMN). Lymphocytes play a decisive role in specific immunity; monocytes and neutrophil granulocytes are cell types that are involved in non-specific immune system defense or inflammatory response. Their task is, e.g., to destroy invading microorganisms that have previously been appropriately identified as foreign by certain endogenous proteins (i.e., by C3b of the complement system or by immunoglobulin IgG).

If the cells have approached the invaded microorganisms, they release oxygen radicals as well as proteases, by which means the microorganisms are killed in order to be phagocytized later. If this reaction is incompletely executed, or if it runs out of control and becomes chronic, also the body's own tissue can be damaged by the release of aggressive oxygen radicals and proteases. During an inflammation, an intensive communication and coordination using, among others, various cytokines, occurs between all cell types. The reaction is very complex and has not been completely elucidated. However, it leads ultimately to the clinically observed inflammatory symptoms of swelling, redness, and fever. An increase in, among others, certain messengers and in monocytes and neutrophil granulocytes, which are produced in the bone marrow and circulate in the blood, is typical. In addition to the pro-inflammatory cytokines mentioned above, the complement proteins C3a and C5a are produced by activation of the proteins C3 and C5, and serve as a measurement of complement activation during the inflammatory or acute-phase reaction.

Currently, extracorporeal therapies are used for several inflammatory diseases, i.e. for colitis ulcerosa, Crohn's disease, and rheumatoid arthritis. According to the prior art, a certain number of cells (presumably especially monocytes and neutrophil granulocytes) are removed from the patient by recirculating the patient's blood extracorporeally and treating it with a cell filter. For example, columns filled with particles or beads of cellulose acetate are used as leukocyte filters. In this case, the removal occurs primarily via cell adsorption of cells on the surface of the beads. Such products are already commercially available. In this case, blood is conducted through a column that contains cellulose acetate beads. The cellulose acetate beads particularly reduce granulocytes and monocytes contained in the blood via adsorption.

U.S. Pat. No. 6,498,007 discloses a method for removal of leukocytes from blood via adsorption onto a carrier. Here, blood is brought into contact with this carrier, preferably in the form of the so-called beads, whereby the carrier shows a higher affinity to infected, activated or defective leukocytes than to uninfected, non-activated or non-defective leukocytes.

Alternatively, non-woven or woven fabrics are used for extracorporeal removal in the leukocyte filter. For example, products based on non-woven fabrics are used for the removal of leukocytes from conserved blood for transfusion (e.g. an erythrocyte or platelet concentrate), in which products the cell removal occurs primarily via mechanical filtration by means of the non-woven fabric. Typically, for transfusions, 500 ml batches of blood are filtered in less than one-half hour. The process is gravity driven and takes place in a single pass and not in circulation. In order that a cell filter may be employed in extracorporeal circulation, approximately 1-6 l of pump-driven blood would have to be filterable for several hours. Polypropylene non-woven fabric in a cylindrical housing with a supply connection at the front end and a discharge connection at the opposite end are commercially available for this. By means of the non-woven fabric used there, leukocytes are retained due to filtration and adsorption effects.

WO 95/18665 discloses a filter and a method for removing leukocytes and virus-inactivating substances from plasma or other blood fractions. The filter is based on a net made of textile fibers. Ligands with a high affinity to virus-inactivating substances or leukocytes are covalently bonded to the net. This method is a selective, yet technically very complex process, because the ligands have to be bonded directly or via linkers to a polymer matrix.

The retention of the leukocytes by such filters is based on cell trapping in the non-woven fabric as well as a more or less strong adsorption of the cells on the fiber surface. However, in these methods the various blood cells are subjected to high mechanical stresses, which can lead to a cell activation or even to destruction of the blood cells.

An essential disadvantage of the existing devices and methods consists in that the various cell types cannot be targeted or specifically adsorbed, and that lymphocytes, thrombocytes, and erythrocytes are adsorbed along with the monocytes and granulocytes. This can be, according to the indication in each case, either unnecessary, or even harmful to the patient. The adsorption of thrombocytes presents a special case. Following activation, thrombocytes play a central role in blood coagulation. This must be counteracted medicinally, such as by means of the administration of heparin as an anticoagulant, so that blood clotting does not occur during the extracorporeal circulation. Blood coagulation that occurs despite the anticoagulant leads to a clogged filter.

A further disadvantage of conventional leukocyte filters is that they are often quite difficult to handle prior to clinical use, e.g., regarding deaeration. Air bubbles in an extracorporeal circulation potentially represent a danger to the patient and are thus highly undesirable. Handling of the filter becomes better and its use becomes safer to the same degree that the possibility of removing air present in the filter becomes simpler.

It is therefore the object of the present invention to make a device available that is easy and efficient to use for reducing the number of leukocytes in blood, in which the disadvantages of the prior art are at least minimized.

This object is achieved by a device for reducing the number of leukocytes in blood comprising a plurality of hollow fibers based on organic polymers, whereby the hollow fibers have a lumen and a wall surrounding the lumen, said wall having an internal surface facing the lumen and an external surface, whereby the hollow fibers are arranged in a cylindrical housing with an inlet arrangement and an outlet arrangement and whereby an outer space is formed between the hollow fibers and the housing, which space is accessible for a fluid via the inlet arrangement and the outlet arrangement, characterized in that only the external surfaces of the hollow fibers are accessible for a fluid, that the lumina of the hollow fibers are not accessible for a fluid, that the arrangement of the fibers shows a high degree of order and that the hollow fibers based on organic polymers cause a generation of the complement activation product C5a in a concentration of at least 10 μg per $m^2$ of fiber surface.

The plurality of hollow fibers based on organic polymers is located in a housing with an inlet arrangement and an outlet arrangement. Thereby, the hollow fibers are so arranged in the housing that an outer space for the blood to flow through is formed around the fibers and delimited by the housing, whereby the inlet arrangement and outlet arrangement on the housing are at the same time executed in such a way that only the outer space around the hollow fibers is capable of supporting fluid flow. The internal surfaces of the hollow fibers facing the lumen and the lumina of the hollow fibers are not accessible in the device of the invention, i.e. the internal surfaces of the hollow fibers cannot be inflowed or flowed through. The housing therefore has no corresponding inlet and/or outlet arrangement for inflowing the internal surfaces.

It is essential for the use of the device of the invention for removing leukocytes from blood that the outer space around the hollow fibers can be flowed through by blood, thus that the hollow fibers can be flowed around at their external surfaces. As has been shown in the not yet published international patent application PCT/EP2006/008585, a flow around the hollow fibers at their external surface provides particular advantages in regard to the adsorption of leukocytes in contrast to a flow through of the lumina of the hollow fibers. It seems probable that the exchange of material of the blood with the internal hollow fiber surface is greatly diminished, due to the laminar flow in the hollow fibers, in comparison with the flow along the external hollow fiber surface.

Accessibility solely at the external surface of the hollow fibers allows on the one hand a simple design of the device of the invention. At the same time, caused by the pressure ratios in the outer space around the hollow fibers blood or blood components are prevented from penetrating the walls of the hollow fibers resulting in agglutination reactions.

The exclusive accessibility of the external surfaces of the hollow fibers and the outer space around the hollow fibers, and therefore the non-accessibility of the lumina of the hollow fibers are realized according to the invention in that the ends of the hollow fibers are sealed. For this purpose, the hollow fiber ends can be embedded in a sealing compound connected with the inner side of the housing, in such a way that the ends of the hollow fibers lie in the sealing compound and are sealed by the sealing compound. In a preferred embodiment of the device of the invention, the hollow fibers can be embedded with their ends separated in the sealing compound, and said fibers can extend essentially rectilinearly between these sealing compounds. In this case, the plurality of hollow fibers is arranged as a fiber bundle of essentially parallel hollow fibers. The bilateral embedding is particularly advantageous with regard to the positioning of the hollow fibers. The hollow fibers can however, also have both ends embedded in the same sealing compound, allowing fluids to circulate around the U-shaped loop which is thus formed. In this case, the hollow fibers can form a loop in their entirety, or each hollow fiber can form its own loop and is embedded with both ends in the same sealing compound. The hollow fibers can also be embedded with only one end, and the other, free end is then sealed, e.g. by welding or gluing, so that the internal surface is not accessible.

The housing can have a constant diameter over its entire length. It is however preferable that the housing has an expanded diameter in the area of the inlet and outlet, which expanded diameter serves as a flow distributor and ensures a uniform blood volume flow across the entire flow cross-section.

Inlet and outlet arrangements can be located in the device of the invention on the housing shell, whereby the inlet arrangement is preferably located at one end of the housing shell and the outlet arrangement at the other end of the housing. The inlet and outlet arrangements can be located on the same side of the housing; however it is more advantageous to locate them on opposing sides, more specifically at an attachment offset by at least 90°, preferably by 180°.

The sealing of the hollow fibers can be implemented through the following means: that they are embedded in a sealing compound, welded or glued. However, embodiments also come within the purview of the invention, in which the hollow fiber ends are not directly sealed, but rather, e.g. embedded in a sealing compound in such a way that the ends are not sealed by the sealing compound, and the hollow fibers are sealed by impermeable housing caps, whereby the lumina of the hollow fibers are not accessible to a fluid.

In a preferred embodiment, the inlet and outlet arrangements can also be located on the end faces of the housing. In the case that the hollow fibers are embedded at their ends in a sealing compound, with the attachment of the inlet and outlet arrangement at the center of the end faces, the plurality of hollow fibers are then embedded in an annular shape with their ends in a sealing compound, whereby the inner diameter of the annular shaped arrangement of hollow fibers should be at least as large as the outer diameter of the inlet and outlet arrangement. The inlet or outlet arrangement is so designed, that it is inserted centrally from the end face through the sealing compound in the housing interior, i.e. in the outer space around the hollow fibers.

Naturally the various possibilities for sealing the hollow fibers and attachment can be combined with each other. Thus, for example, inlet or outlet arrangement on the end face at one end of the housing can be combined with an inlet or outlet arrangement located laterally on the other end of the housing shell. It is also possible that the hollow fiber ends are embedded at the inlet side and only be sealed by gluing or welding on the outlet side and otherwise lie freely. The housing side on which the free ends of the hollow fibers lie can be sealed by an end cap, whereby the inlet or outlet arrangement can be attached either on the housing shell or on the face at the end cap, or inserted through the sealing compound.

In a further preferred embodiment, the hollow fibers lie in several layers of parallel hollow fibers, whereby the layers of parallel hollow fibers are executed especially preferred as mats. The hollow fibers within each mat are held by several transverse fibers applied by a weaving or knitting process. Arrangements of this type of parallel hollow fibers are described e.g. in EP 285 812. The hollow fiber mat comprises in an especially preferred embodiment one single hollow fiber positioned in a meandering course which is likewise held by several transverse fibers applied by weaving or knitting processes. In this arrangement, only the two ends of the hollow fiber have to be sealed for the entire mat so that the entire interior surface is not accessible.

The hollow fiber mats used in the device of the invention can be superimposed on each other in several layers, preferably 10-200 mat layers, whereby each mat layer preferably contains 3-30 hollow fibers per cm. The parallel hollow fibers of one mat layer preferably intersect with the hollow fibers of the adjacent mat layer at an angle between 10° and 90°, especially preferably at an angle between 10° and 40°. The ends of the hollow fibers are embedded in sealing compounds, said ends being preferably separated, and said ends are impermeably sealed by these sealing compounds. This preferred embodiment of the device of the invention distinguishes itself by a particularly low pressure loss. In addition, the intersecting mat layers ensure an excellent flow distribution and a uniform blood film thickness during use of the inventive device.

The hollow fiber mats can be executed as a wound body for use in the device of the invention, and can be arranged in a cylindrical housing with a circular cross-section. The hollow fibers can be embedded in sealing compound in such a way that the hollow fiber ends lie within the sealing compound and are sealed by this. In this embodiment it is also, however, sufficient if the housing is sealed with end caps or sealing compound and the hollow fiber mat is only inserted in the housing, whereby the ends of the hollow fibers have to be sealed, e.g. by gluing or welding, if these are not embedded in the sealing compound.

In order to prevent the flow channels between the hollow fibers from becoming too narrow or too small, and thus forming areas that cannot be flowed through, the external diameter of the hollow fibers is at least 150 μm in a preferred embodiment of the device of the invention, and preferably at least 250 μm. Hollow fibers of this type are easy to handle and at the same time characterized by a low weight and low material costs, due to their hollow structure, and in spite of the required minimum diameter. It is further preferred that the external diameter of the hollow fibers does not exceed 2000 μm, as otherwise the surface available for adsorption is too low in relation to volume.

In order to guarantee that all of the hollow fibers equally come into contact with the blood flowing along the hollow fibers, the hollow fibers in a preferred embodiment of the inventive device can also be arranged spaced apart from each other, for example using so-called spacer yarns. With regard to avoiding a sieve effect, a separation of the fibers is particularly advantageous. Spacer yarns of this type is particularly advantageous, because a uniform distance between the essentially parallel-lying hollow fibers is guaranteed thereby. Arrangements with this type of spacer yarns are described for example in EP 732 141 or in EP 285 812. Preferably, the spacer yarns consist of the same material as the plurality of parallel fibers. It is, however also possible, by using a different fiber material for the spacer yarn, to reduce the number of additional cell types present in the blood.

In order to avoid damage to the cells contained in the blood, it is important that the blood does not significantly penetrate the hollow-fiber material, and that it does not flow through the hollow-fiber material. This is achieved on the one hand by sealing the hollow fibers, and on the other by preferably using hollow fibers that have an impermeable surface, or in the case of a porous surface, that has a maximum pore size of 0.1 μm.

Hollow fiber membranes with impermeable or porous structures are best suited as hollow fibers. Membranes of these types are used, for example, for blood treatment during dialysis. In this case, the pore size of the hollow fiber membranes should be selected, in such a way that the membrane wall cannot be flowed through by the blood, i.e., the blood essentially cannot penetrate into the hollow fibers or into the hollow fiber membrane.

The number of hollow fibers in the device of the invention lies preferably in the range of 2000 to 20,000 hollow fibers, particularly preferably in the range of 4000 to 14,000 hollow fibers.

The fill ratio of the housing with the hollow fibers based on organic polymers should be between 10% and 70%, preferably between 30% and 60%. Since the fibers, depending on the fiber material, can swell strongly in varied levels when in contact with liquids, the determination of the fill ratio of the housing is to be established using fibers in their swollen state. Significant differences relating to fiber diameter in swollen and non-swollen states are observed in fibers that strongly swell, such as, for example, in those based on cellulose. Due to the swelling, different fill ratios therefore result when the fibers are present in their dry state. Fibers that do not, or do not appreciably swell, such as those made of polysulfone, show, in contrast, little or no difference in their swollen and not-swollen states for the determination of the fill ratio.

The fill ratio of the housing is to be limited to the given range, on the one hand to make a sufficiently large fiber surface available, on the other hand to avoid a sieve effect in the reduction in the number of leukocytes in the inventive method.

The device of the invention preferably has a length to diameter ratio of at least 3:1, particularly preferably of at least 5:1. Especially good results are achieved with devices that have a length to diameter ratio of at least 10:1. By this means, it can be guaranteed during use that the contact period is sufficiently long and the flow velocity of the blood through the device of the invention is not too low.

In the sense of the present invention, a high degree of order is understood to mean that the fibers lie in a similar arrangement with each other, or that a large proportion of the fibers are arranged next to each other along their extension direction. The fibers are not arranged like non-woven fabrics, random fibers, or random laid fiber mats, instead the arrangement of the fibers has a regular structure. Theoretically, a bundle of straight fibers, which lie parallel to each other, has the highest degree of order. A bundle of corrugated or crimped fibers, in which the fibers all show the same extension direction, also has a high degree of order in the sense of the present invention. In the sense of the present invention, a fiber bundle that is laid in a loop also has a high degree of order. In this case, the arrangement of the fibers to each other is also similar. Additionally, a high degree of order means that at least 30% of the fibers lie parallel. Furthermore, this includes fibers that are present in several layers, whereby the fibers are arranged essentially parallel to each other within each layer. The parallel fibers in one layer can, however, cross the parallel fibers in another layer. Arrangements of this type are described in EP 285 812. Non-woven fabrics or random laid fiber mats, in which the fibers are completely without order and mixed with each other, do not constitute the arrangement with a high degree of order according to the invention. In comparison with non-woven fabrics, the arrangement of the fibers with a high degree of order in accordance with the invention shows a greater surface area and, when used in the method of the invention, a uniform blood film thickness. The high degree of order ensures that the blood flowing past the fibers shows comparably low turbulence and the cells contained in the blood are exposed to a lower shear stress. Additionally, the high degree of order ensures that the formation of dead spaces and preferred channels, so called shunts, is largely prevented. By this means, a particularly gentle blood treatment is achieved.

The high degree of order also ensures that the reduction in the number of leukocytes is essentially not produced by a sieve effect, as this would be the case, e.g., with a non-woven fabric, but rather by adsorption effects, by which means an especially gentle blood treatment is made possible. Additionally, the sieve effect that appears in the case of a non-woven fabric also inevitably causes an undesired reduction in other cellular blood components, e.g., thrombocytes. It is therefore preferred that the plurality of hollow fibers are arranged with essentially parallel fibers as a fiber bundle.

C5a is a cleavage product of the plasma protein C5. The maximum value of the C5a concentration in blood is therefore limited by the concentration of C5 in the blood plasma, whereby the C5 concentration in the plasma is subject to large individual fluctuations and can be from approximately 40 mg/l to 150 mg/l. Based on the molar mass ratio of C5 to C5a, this results therefore in a theoretical maximum concentration of 9 mg/l C5a in the blood.

The concentration of the complement activation product C5a in blood plasma is determined by using a sandwich ELISA (Enzyme Linked Immunosorbent Assay) produced by DRG Diagnostics in Marburg, Germany. After contact of the fibers with human donor blood (5 U/ml heparin), 1.8 ml of blood is removed at various times and is stopped with 0.2 ml of a 100 mM EDTA solution. Prior to the analysis, in accordance with the manufacturer's instructions, the C5 needs to be precipitated (200 µl plasma+200 µl precipitate reagent). 50 µl of supernatant is used in the determination. The detection sensitivity of the assay lies at <0.02 µg/l, the recovery rate of C5a in the plasma at 86-114% and the coefficient of variation at 5-8% (intra-assay) and 6-10% (inter-assay). The C5a concentration measured is dependent on the blood volume and the fiber surface. Therefore, for the determination of the C5a concentration in relation to the external surface of the fibers, the absolute C5a content in the sample must be determined and placed in relation to the external fiber surface. Thereby, a ratio of blood volume (V) to fiber surface area (A), V/A, of 0.3 L/m$^2$ is to be maintained. The determination of the area-related C5a concentration occurs after a treatment period of 3 hours, that is, the blood sample is channeled for 3 hours along the external surface of the fibers, during which a linear flow rate of 5 to 30 cm/min must be maintained. Because the test results are subject to donor-dependent, individual fluctuations, the number of samples N should amount to at least 2, and the average values of the samples should be stated.

Without wishing to be bound by the theory, it is assumed that an important relevance is accorded to complement activation in the treatment of inflammatory diseases, and that a reduction in the number of leukocytes in combination with a complement activation is significantly more effective than a reduction in the number of leukocytes alone. For this to occur, the complement activation, determined by the concentration of C5a in the blood, must lie above the threshold value according to the invention.

A connection between the parameters leukocyte count and C5a is probably due to the fact that certain leukocytes can be activated by C5a. The activation by C5a and other factors has the effect that the cells become more adhesive (stickier) and therefore bond more strongly to C5a generating surfaces.

It is therefore preferred that the hollow fibers cause a further increased generation of the complement activation product C5a in a concentration of at least 75 µg per m$^2$ of fiber surface.

It is especially preferred that the hollow fibers cause a generation of the complement activation product C5a in a concentration of at least 100 µg per m$^2$ of fiber surface.

Since the required generation of the C5a is not only dependent on the polymer, but also on admixtures or on the degree of substitution of the polymer, the term 'based on organic polymers' comprises the polymer materials as such, substitutions and mixtures thereof, copolymers of these materials as well as any added auxiliary materials or additives, e.g., hydrophilizing agents.

Preferably the arrangement of the hollow fibers has a specific surface area for blood treatment of between 0.1 and 100 cm$^2$ of fiber surface per ml of blood to be treated, preferably between 0.5 and 20 cm$^2$ of fiber surface per ml of blood to be treated. The amount of the blood to be treated results from the duration of the blood treatment and the volumetric flow rate.

Hollow fibers made from organic polymers can be hollow fibers made from natural polymers or from polymers that were produced synthetically. Hollow fibers made from natural polymers are particularly those based on cellulosic polymers, which also comprises hollow fibers that were subjected to so-called polymer-analog reactions. Examples of such hollow fibers based on cellulose are those made from regenerated cellulose, cellulose acetate, or modified cellulose, such as, e.g., cellulose ester, cellulose ether, cellulose modified with benzyl groups (benzyl cellulose) or cellulose modified with diethylaminoethyl or mixtures of these cellulosic polymers. In the method of the invention, a large reduction in the number of leukocytes is achieved with hollow fibers based on cellulosic polymers; a particularly large reduction is obtained with hollow fibers made of regenerated cellulose. Furthermore, hollow fibers based on chitin or chitosan can be used.

Organic polymers include polymers that are produced using synthetic means. Hollow fibers made of synthetic polymers of the following type can be used: those that consist of polyolefins, polyamides, polyacrylonitrile, polycarbonates or polyesters as well as modifications, blends, mixtures or copolymers of these polymers. Preferably, those polymers are used that are based on sulfone polymers, such as polysulfone or polyether sulfone. These polymers can be admixed with additional polymers like polyethylene oxide, polyhydroxyether, polyethylene glycol, polyvinyl alcohol or polycaprolactone as additives. The hollow fibers can have, in addition to this, a coating with an additive. Such hollow fibers preferably contain a hydrophilizing agent, e.g., polyvinylpyrrolidone, or a hydrophilic modification of this polymer.

The device of the invention is obviously suitable not only for the reduction in the number of leukocytes in whole blood, but also for the reduction in the number of residual leukocytes in blood plasma or other blood concentrates. Therefore, within the context of the present invention, blood is understood to mean whole blood, blood plasma, or a blood concentrate.

It has been demonstrated that primarily leukocytes are reduced using the indicated fiber materials. Using in particular cellulosic fiber materials, the number of granulocytes and monocytes is primarily reduced. Lymphocytes are only negligibly reduced with cellulosic materials.

It is therefore possible within the context of the method of the invention to specifically reduce certain cell types from a class, such as the monocytes and granulocytes, but not the lymphocytes, from the class of leukocytes. Further, fiber materials based on cellulose distinguish themselves in that thrombocytes are only retained in low amounts.

In certain applications, it could be advantageous to also specifically remove thrombocytes from the blood. For these applications, fibers made of polyethylene terephthalate (PET), polysulfone or polyether sulfone are suitable. Should a reduction in thrombocytes and leukocytes be desired, a combination of, for example, cellulosic fibers and PET fibers lends itself to the device of the invention.

The inventive device for removing leukocytes from blood will be explained in more detail based on the following figures. The figures show preferred embodiments of the device of the invention, which embodiments are, however, not understood to be limiting.

Figure 1A:
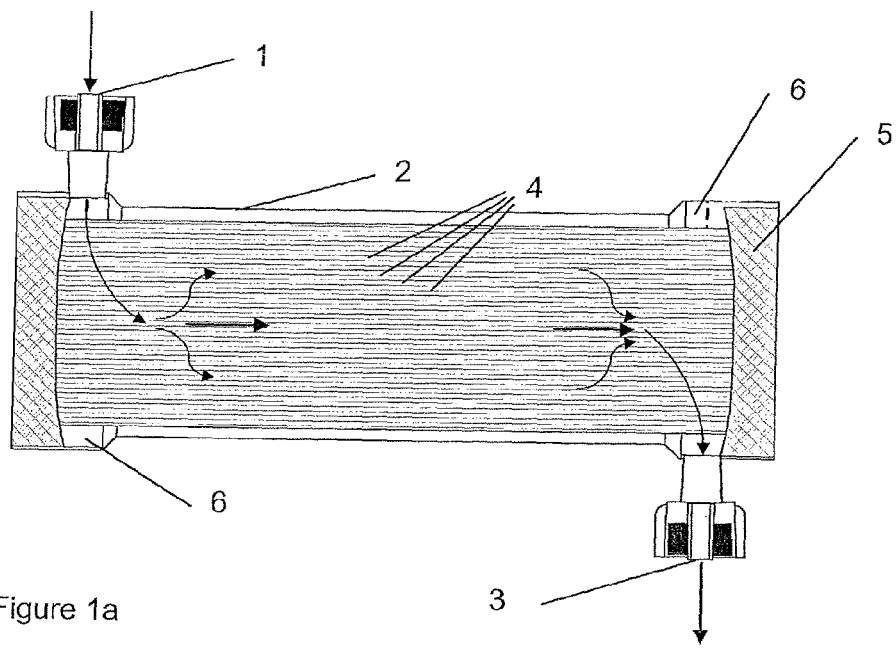
FIG. 1a, 1b show preferred embodiments of the device of the invention with inlet and outlet arrangements on the housing shell.

FIG. 1a shows a preferred embodiment of the device of the invention with inlet and outlet arrangements on the housing shell. The inlet arrangement 1 is located at one end of the housing shell 2 in this embodiment and the outlet arrangement 3 is attached at a 180° offset at the other end of the housing shell. The Luerlock connections shown can be used, e.g. for the inlet and/or outlet arrangement; however all other connections known to one skilled in the art can also be used.

The ends of the hollow fibers 4 are embedded in a sealing compound 5 connected with the interior side of the housing, so that the ends of the hollow fibers 4 lie in the sealing compound 5 and are sealed by the sealing compound 5. The lumina of the embedded hollow fibers 4 are not accessible, instead only the external surface of the follow fibers. The hollow fibers 4 are embedded with their ends separated in sealing compounds 5 in the preferred embodiment shown, and said fibers extend essentially parallel between these sealing compounds 5. Flow distributors 6 are located in the area of the inlet arrangement 1 and the outlet arrangement 3, in the form of an expanded housing diameter at these points, to ensure better blood distribution.

Figure 1B:
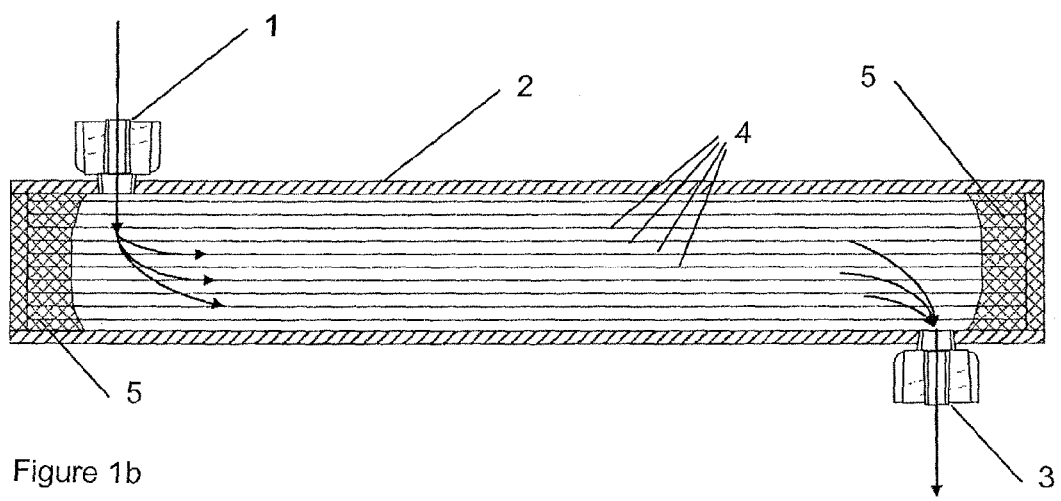

FIG. 1*b* shows a further preferred embodiment of the device of the invention with inlet arrangement 1 and outlet arrangement 3 at the housing shell and with a larger, in comparison with FIG. 1*a*, length/diameter ratio of approximately 6:1

Figure 2:
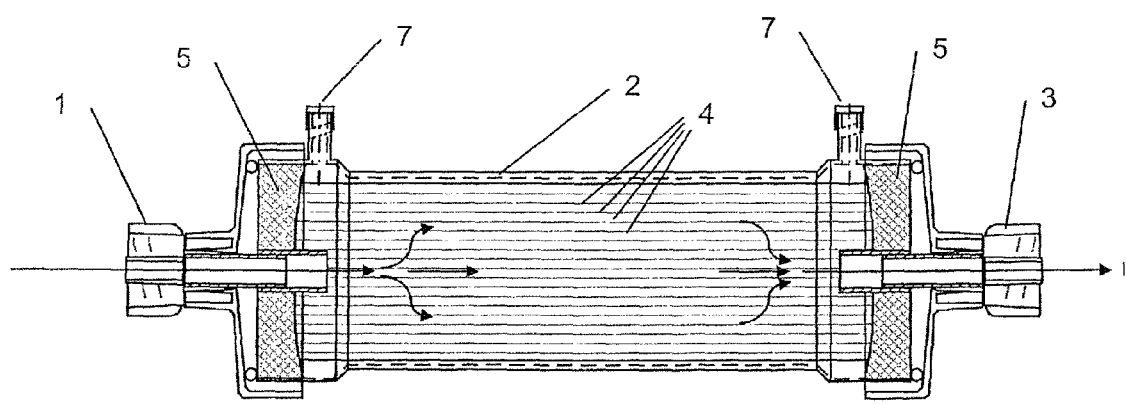
FIG. 2 shows a preferred embodiment of the device of the invention with an inlet and/or outlet arrangement on the face.

FIG. 2 shows a preferred embodiment of the device of the invention with inlet arrangement 1 and outlet arrangement 3 attached in the center of the faces of the housing. In this case the inlet arrangement 1 and the outlet arrangement 3 are also realized with Luerlock connections, however, all other connections known to one in the art could be used. The hollow fibers 4 are also embedded with their ends separately in sealing compounds 5 in this preferred embodiment and said hollow fibers extend essentially parallel between these two sealing compounds 5. Due to the location of the inlet and outlet arrangements on the faces, the plurality of hollow fibers 4 is embedded in sealing compound in an annular shape with their ends around the inlet or outlet arrangement. Connections 7 on the housing shell 2 shown in FIG. 2 are sealed, but could be used during use of the device or also for venting the device. The inlet and outlet arrangement, respectively is designed in such a way that it is inserted centrally from the face through the sealing compound into the interior of the housing, i.e. in the outer space around the hollow fibers. For better distribution of the blood, the inlet arrangement 1 and also the outlet arrangement 3 can be implemented as a perforated tube in the interior of the housing, whereby the tubular end of the inlet or outlet arrangement is then sealed, so that the fluid flowing in can only flow via the perforated shell into the outer space around the hollow fibers.

The invention claimed is:

1. A device for reducing the number of leucocytes in blood comprising a plurality of hollow fibers (4) based on organic polymers, whereby the hollow fibers (4) have a lumen and a wall surrounding the lumen, said wall having an internal surface facing the lumen and an external surface, whereby the hollow fibers are arranged in a cylindrical housing with an inlet arrangement (1) and an outlet arrangement (3) and whereby an outer space is formed between the hollow fibers (4) and the housing, which space is accessible for a fluid via the inlet arrangement (1) and the outlet arrangement (3), characterized in that only the external surfaces of the hollow fibers (4) are accessible for a fluid, that the lumen of the hollow fibers (4) are not accessible for a fluid, that the arrangement of the hollow fibers (4) shows a high degree of order and that the hollow fibers (4) based on organic polymers cause a generation of the complement activation product C5a in a concentration of at least 10 µg per m$^2$ of fiber surface.

2. The device for reducing the number of leukocytes in blood according to claim 1, characterized in that the hollow fibers are sealed at their ends by embedding in a sealing compound, by welding or gluing.

3. The device for reducing the number of leukocytes in blood according to claim 2, characterized in that the ends of the hollow fiber are embedded in such a way in a sealing compound connected with the inner side of the housing, that the ends of the hollow fibers lie in the sealing compound and are sealed by the sealing compound, and that the hollow fibers are embedded with their ends separated in sealing compounds, and said fibers extend essentially rectilinearly between these sealing compounds.

4. The device for reducing the number of leukocytes in blood according to claim 1, characterized in that the inlet arrangement is located at one end of the housing shell and the outlet arrangement is located at the other end of the housing.

5. The device for reducing the number of leukocytes in blood according to claim 1, characterized in that the inlet or outlet arrangement is designed in such a way that it is inserted centrally from the face through the sealing compound into the interior of the housing, i.e. in the outer space around the hollow fibers.

6. The device for reducing the number of leukocytes in blood according to claim 1, characterized in that the fiber diameter of the fibers based on organic polymers lies between 150 µm and 2000 µm.

7. The device for reducing the number of leukocytes in blood according to claim 1, characterized in that the hollow fibers are hollow fibers with impermeable or porous structures and that the hollow fibers with porous structure have a maximum pore size of 0.1 µm.

8. The device for reducing the number of leukocytes in blood according to claim 1, characterized in that a fill ratio of the fibers in the housing lies in the rant of 10% to 70%.

9. The device for reducing the number of leukocytes in blood according to claim 1, characterized in that the hollow fibers based on organic polymers are arranged in one or several layers and that the fibers within one layer lie essentially parallel.

10. The device for reducing the number of leukocytes in blood according to claim 1, characterized in that the hollow fibers cause a generation of the complement activation product C5a in a concentration of at least 75 µg of blood per m$^2$ of fiber surface.

11. The device for reducing the number of leukocytes in blood according to claim 1, characterized in that the hollow fibers based on organic polymers consist of regenerated cellulose, cellulose acetate, or cellulose modified with benzyl groups (benzyl cellulose).

12. The device for reducing the number of leukocytes in blood according to claim 1, characterized in that the hollow fibers based on organic polymers consist essentially of polyether sulfone or polysulfone.

13. The device for reducing the number of leukocytes in blood according to claim 1, characterized in that the arrangement of a plurality of fibers also contains fibers made of polyethylene terephthalate.

* * * * *